US00PP31460P2

(12) United States Plant Patent
Christensen

(10) Patent No.: US PP31,460 P2
(45) Date of Patent: Feb. 18, 2020

(54) ***PEPEROMIA* PLANT NAMED 'BRASILIA'**

(50) Latin Name: *Peperomia caperata*
Varietal Denomination: Brasilia

(71) Applicant: Gartneriet Tingdal Aps, Odense S (DK)

(72) Inventor: Per Siggaard Christensen, Odense S (DK)

(73) Assignee: Gartneriet Tingdal Aps, Odense (DK)

( * ) Notice: Subject to any disclaimer, the term of this patent is extended or adjusted under 35 U.S.C. 154(b) by 0 days.

(21) Appl. No.: 16/501,077

(22) Filed: Feb. 20, 2019

(51) Int. Cl.
*A01H 5/00* (2018.01)

(52) U.S. Cl.
USPC ..... Plt./373

(58) Field of Classification Search
USPC ..... Plt./373
CPC ..... A01H 5/00
See application file for complete search history.

*Primary Examiner* — Annette H Para

(57) ABSTRACT

A new cultivar of *Peperomia* plant named 'Brasilia' that is characterized by leaves that are grey-purple on the upper surface and red on the lower surface, a large number of leaves, yellow-white flower spikes and a compact habit.

1 Drawing Sheet

Botanical classification: *Peperomia caperata.*
Variety denomination: 'Brasilia'.

BACKGROUND OF THE INVENTION

The present invention relates to a new and distinct cultivar of *Peperomia* plant botanically known as *Peperomia caperata* and hereinafter referred to by the cultivar name 'Brasilia'.

'Brasilia' originated from the crossing of the female or seed parent, *Peperomia caperata* 'Teresa' (not patented) and the male or pollen parent, *Peperomia* 'Eden Rosso' (U.S. Plant Pat. No. 24,379). The crossing was conducted in 2015in Odense, Denmark. The resulting seeds were subsequently planted and grown. The cultivar 'Brasilia' was selected by the inventor in 2016 in a controlled environment as a single plant within the progeny of the stated cross in a cultivated area of Odense, Denmark.

Asexual reproduction of the new cultivar 'Brasilia' first occurred by leaf cuttings in 2016in Odense, Denmark. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Peperomia* cultivar 'Brasilia'. These traits in combination distinguish 'Brasilia' as a new and distinct cultivar apart from other existing varieties of *Peperomia* known by the inventor.

1. *Peperomia* 'Brasilia' exhibits leaves that are grey-purple on the upper surface and red on the lower surface.
2. *Peperomia* 'Brasilia' exhibits a large number of leaves.
3. *Peperomia* 'Brasilia' exhibits yellow-white flower spikes.
4. *Peperomia* 'Brasilia' exhibits a compact habit.

The closest comparison cultivars are *Peperomia* 'Schumi Red' (not patented) and *Peperomia* 'Kirsten' (not patented). 'Brasilia' is distinguishable from 'Schumi Red' by the following characteristics:

1. *Peperomia* 'Brasilia' exhibits leaves that are grey-purple on the upper surface and red on the lower surface. In comparison, the leaves of 'Schumi Red' are red on both the upper and lower surfaces.
2. *Peperomia* 'Brasilia' exhibits a less compact plant habit than the plant habit of 'Schumi Red'.

'Brasilia' is distinguishable from 'Kirsten' by the following characteristics:

1. *Peperomia* 'Brasilia' exhibits leaves that are grey-purple on the upper surface and red on the lower surface. In comparison, the leaves of 'Kirsten' are green with silver lines on the upper surface and green on the lower surface.

'Brasilia' is distinguishable from the female parent plant, by the following characteristics:

1. The leaves of 'Brasilia' are grey-purple on the upper surface and red on the lower surface. In comparison, the leaves of the female parent plant are grey on both the upper and lower surfaces.
2. The leaves of 'Brasilia' are smaller than the leaves of the female parent plant.

'Brasilia' is distinguishable from the male parent plant by the following characteristics:

1. The leaves of 'Brasilia' are grey-purple on the upper surface and red on the lower surface. In comparison, the leaves of the male parent plant are dark green on the upper surface and red on the lower surface.
2. The leaves of 'Brasilia' are larger than the leaves of the male parent plant.
3. The leaves of 'Brasilia' do not have ribs or riffles. In comparison, the leaves of the male parent plant have ribs and riffles.

BRIEF DESCRIPTION OF THE DRAWING

The accompanying photograph illustrates the distinguishing traits of *Peperomia* 'Brasilia'. The photograph shows an overall view of a 30 week old plant.

The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Peperomia* cultivar named 'Brasilia'. Data was collected in Odense, Denmark from 30 week old plants grown in a glass greenhouse in 13.0 cm. diameter containers. The time of year was Winter and the temperature range was 20-23 degrees Centigrade during the day and 18-20 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'Brasilia' has not been tested under all possible conditions and phenotypic differences may be observed with variations in environmental, climatic, and cultural conditions, however, without any variance in genotype.

Botanical classification: *Peperomia caperata* 'Brasilia'.
Annual or perennial: Perennial.
Parentage: 'Brasilia' is a hybrid of the female parent, Peperomia 'Teresa' and the male parent Peperomia 'Eden Rosso'.
Plant type: Potted plant.
Growth habit: Rosette of leaves forming very short thick stems.
Plant shape: Flattened globe shaped.
Suitable container size: 7 cm. pots or larger.
Plant height to top of foliage: Average 16.0 cm.
Plant height to top of floral plane: Average 15.6 cm.
Plant width: Average 35.4 cm.
Vigor: Moderate.
Growth rate: Moderate.
Low Temperature Tolerance: 10° Centigrade.
High Temperature Tolerance: 35° Centigrade.
Propagation: Leaf cuttings.
Time to initiate roots (summer): 28 days at 20° C.
Time to initiate roots (winter): 35 days at 20° C.
Time to produce a rooted cutting (summer): 80 days at 20° C.
Time to produce a rooted cutting (winter): 100 days at 20° C.
Crop time: Approximately 30 weeks in Odense, Denmark.
Root system: Fibrous.
Plant fragrance: None.
Stem:
- *Branching habit.*—Very short thick main stems branching into lateral rosettes of leaves.
- *Pinching.*—Not required.
- *Number of main stems per plant.*—Average 8.
- *Number of lateral branches per plant.*—Average 32.
- *Lateral branch dimensions.*—Average 2.8 cm. in length and 0.8 cm. in width.
- *Internode length.*—Less than 0.1 cm.
- *Stem appearance.*—Succulent.
- *Stem shape.*—Rounded.
- *Stem texture.*—Smooth.
- *Stem luster.*—Slightly glossy.
- *Stem pubescence.*—Absent.
- *Stem angle.*—Average 20 degrees.
- *Stem strength.*—Moderately strong.
- *Stem color* (*young*).—148A.
- *Stem color* (*mature*).—Between 148A and 197A.
- *Internode color.*—Between 148A and 197A.

Foliage:
- *Leaf arrangement.*—Alternate.
- *Compound or single.*—Single.
- *Quantity of leaves per lateral branch.*—Average 8.
- *Leaf shape.*—Ovate.
- *Leaf aspect.*—Strongly concave.
- *Leaf apex.*—Broad acute to broad apiculate.
- *Leaf base.*—Hastate, lobes touching to slightly overlapping.
- *Leaf dimensions.*—Average 7.0 cm. in length and 5.0 cm. in width.
- *Texture.*—Glabrous, moderately to strongly leathery (both surfaces).
- *Leaf luster upper surface.*—Glossy.
- *Leaf luster lower surface.*—Moderately glossy.
- *Pubescence.*—Absent (both surfaces).
- *Leaf margin.*—Entire.
- *Leaf lobed.*—Not lobed.
- *Leaf rugose.*—Not rugose (both surfaces).
- *Venation pattern.*—Parallel, strongly furrowed.
- *Young leaf color* (*upper surface*).—N200A.
- *Young leaf color* (*lower surface*).—Between N77C and N186C.
- *Mature leaf color* (*upper surface*).—Between 147A and N189A.
- *Mature leaf color* (*lower surface*).—183B.
- *Vein color* (*upper surface*).—Between 147A and N189A.
- *Vein color* (*lower surface*).—Between 183A and 200C.

Petiole:
- *Petiole dimensions.*—Average 9.6 cm. in length and 0.4 cm. in diameter.
- *Petiole texture.*—Glabrous.
- *Petiole luster.*—Moderately glossy on both sides.
- *Petiole pubescence.*—Absent.
- *Petiole strength.*—Low.
- *Petiole color* (*both sides*).—N148D with fine stripes 181A, stripes more dense toward distal end.

Flower:
- *Inflorescence type.*—Axillary spike.
- *Inflorescence dimensions.*—Average 5.1 cm. in length and 0.5 cm. in diameter.
- *Quantity of flowers per inflorescence.*—Average over 1,000.
- *Quantity of flowers per plant.*—Average over 1,500.
- *Quantity of buds per plant.*—Average over 8,500.
- *Quantity of flowers and buds per plant.*—Average over 10,000.
- *Fragrance.*—None.
- *Bud length.*—Average 0.4 mm.
- *Bud diameter.*—Average 0.4 mm.
- *Bud shape.*—Flattened globe shaped.
- *Bud texture.*—Glabrous.
- *Bud luster.*—Slightly glossy.
- *Bud color.*—145B, dotted 181B.
- *Flower type and form.*—Flowers have no petals or sepals and consist of two stamens, one pistil and one bract below the reproductive organs.
- *Flower aspect.*—Outward.
- *Flower shape.*—Rotate, two stamens, one pistil and one bract located below the stamens and pistil.

*Flower dimensions.*—Average 0.75 mm. in height (excluding bract) and 0.75 mm. in diameter.
*Flower longevity.*—Approximately 1 month.
*Natural flowering season.*—Late winter to late spring.
*Persistent or self-cleaning.*—Self-cleaning.

Bracts:
*Bract arrangement.*—A single bract is located below the stamens and pistil.
*Bract dimensions.*—Average 0.5 mm. in length and 0.5 mm. in width.
*Bract shape.*—Orbicular.
*Bract color.*—145B to 145C, finely dotted 181B to 181C.

Peduncle:
*Peduncle dimensions.*—Average 11.6 cm. in length and 0.3 cm. in diameter.
*Peduncle angle.*—30 degrees from vertical.
*Peduncle strength.*—Moderately weak.
*Peduncle texture.*—Smooth.
*Peduncle luster.*—Moderately glossy.
*Peduncle color.*—N148D with fine stripes 183C, stripes denser toward distal end.

Reproductive organs:
*Stamen number.*—2.
*Anther shape.*—Kidney shaped.
*Anther length.*—Average 0.2 mm.
*Anther width.*—Average 0.15 mm.
*Anther color.*—158C to 158D.
*Filament length.*—Average 0.15 mm.
*Filament color.*—145C to 145D.
*Amount of pollen.*—Low.
*Pollen color.*—155A.
*Number of pistils.*—1.
*Pistil length.*—Average 0.75 mm.
*Stigma shape.*—Flattened, rounded.
*Stigma dimensions.*—0.05 mm. in length and 0.05 mm. in diameter.
*Stigma color.*—157A.
*Style length.*—Average 0.7 mm.
*Style color.*—145C.
*Ovary color.*—145D.

Fruit and seed: 'Brasilia' has not produced fruit or seed to date.

Disease and pest resistance: Disease and pest resistance has not been observed.

The invention claimed is:

1. A new and distinct variety of *Peperomia* plant named 'Brasilia' as described and illustrated.

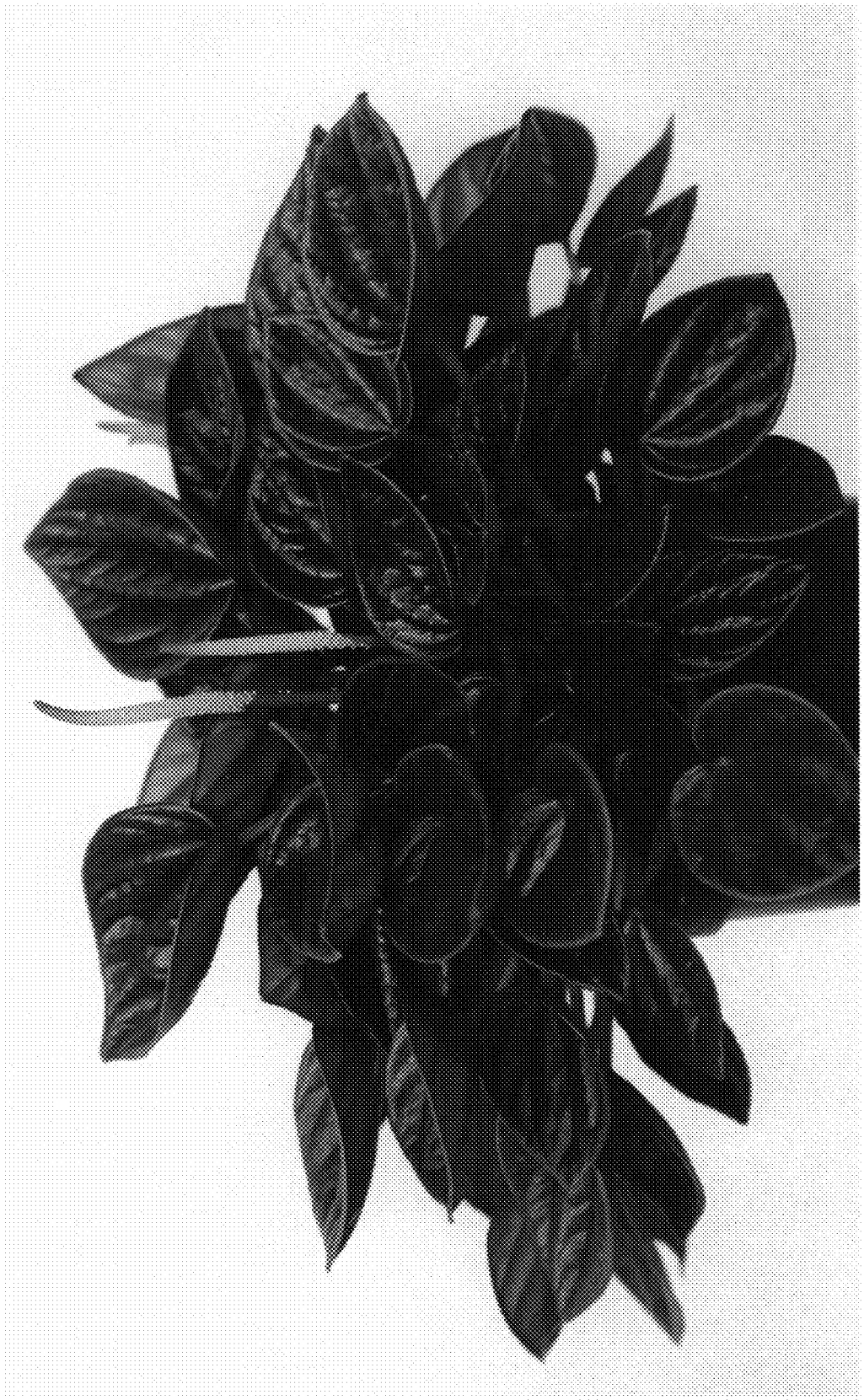

* * * * *